(12) United States Patent
Lin et al.

(10) Patent No.: US 12,733,813 B2
(45) **Date of Patent: *Sep. 15, 2026**

(54) DEVICES AND METHODS FOR IN VIVO TISSUE DIAGNOSIS

(71) Applicants: Wei-Chiang Lin, Miami, FL (US); Anamika Prasad, Miami, FL (US)

(72) Inventors: Wei-Chiang Lin, Miami, FL (US); Anamika Prasad, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/261,449

(22) Filed: Jul. 7, 2025

(65) Prior Publication Data

US 2026/0083331 A1 Mar. 26, 2026

Related U.S. Application Data

(63) Continuation of application No. 18/894,921, filed on Sep. 24, 2024, now Pat. No. 12,433,489.

(51) Int. Cl.
*A61B 5/00* (2006.01)

(52) U.S. Cl.
CPC ............ *A61B 5/0075* (2013.01); *A61B 5/441* (2013.01); *A61B 5/442* (2013.01)

(58) Field of Classification Search
None
See application file for complete search history.

(56) References Cited

U.S. PATENT DOCUMENTS

| | | | | |
|---|---|---|---|---|
| 5,561,521 | A * | 10/1996 | Chase | G01J 3/4535 356/451 |
| 8,172,459 | B2 * | 5/2012 | Abreu | A61B 5/6814 374/208 |
| 2015/0141854 | A1 * | 5/2015 | Eberle | A61B 5/02154 600/488 |
| 2024/0102903 | A1 * | 3/2024 | Cui | G01N 3/066 |

* cited by examiner

*Primary Examiner* — Keith M Raymond
*Assistant Examiner* — Michael S Kellogg
(74) *Attorney, Agent, or Firm* — SALIWANCHIK, LLOYD & EISENSCHENK

(57) ABSTRACT

Systems, devices, and methods for in vivo tissue diagnosis are provided. Optical spectroscopy can be utilized to characterize the morphological and/or compositional characteristics of in vivo tissue, and an indentation method can be used to measure the mechanical characteristics of the tissue. These intrinsic properties can then be used to detect disease and/or injury development in the in vivo tissue. A portable, handheld device can be used to perform the optical spectroscopy and/or the indentation method.

14 Claims, 11 Drawing Sheets

DEVICES AND METHODS FOR IN VIVO TISSUE DIAGNOSIS

CROSS-REFERENCE TO RELATED APPLICATION

The present application is a continuation application of U.S. application Ser. No. 18/894,921, filed Sep. 24, 2024, the disclosure of which is hereby incorporated by reference in its entirety, including all figures, tables, and drawings.

BACKGROUND

Current skin cancer screening methods often fall short in early detection due to several key limitations, including limited accessibility and frequency of screenings, subjective assessments that can lead to inconsistent diagnoses, and technological shortcomings that reduce sensitivity and specificity. Existing methods may also be biased against darker skin tones and are often costly, deterring routine checks. These challenges contribute to delayed diagnoses and reduced effectiveness of early interventions.

BRIEF SUMMARY

Embodiments of the subject invention address the challenges discussed in the Background section by providing novel and advantageous systems, devices, and methods for in vivo tissue diagnosis. Optical spectroscopy can be utilized to characterize the morphological and/or compositional characteristics of in vivo tissue, and an indentation method can be used to measure the mechanical characteristics of the tissue. These intrinsic properties can then be used to detect disease and/or injury development in the in vivo tissue. The systems and methods can include a portable (e.g., handheld) tool to perform the optical spectroscopy and/or the indentation method.

In an embodiment, a device for in vivo tissue diagnosis can comprise: a cantilever beam; an indenter comprising a first end connected to the cantilever beam and an indenter tip at a second end opposite from the first end of the indenter; a light source configured to provide light; at least one optical fiber disposed on the cantilever beam, the light provided by the light source traveling through the at least one optical fiber; and a light sensor configured to sense the light provided by the light source. The device can further comprise a main housing in which the cantilever beam is disposed. The light source can be disposed at a first end of the main housing, and the light sensor can be disposed at a second end of the main housing opposite from the first end of the main housing. The main housing can comprise a hole through which the indenter protrudes. The indenter tip can be, for example, a spherical indenter tip. The at least one optical fiber can comprise a plurality of optical fibers, and at least one optical fiber of the plurality of optical fibers can be disposed within the indenter. The indenter can comprise an excitation optical fiber and an emission optical fiber disposed therein, and the indenter tip can comprise two holes through which light from the excitation optical fiber exits and through which light is collected by the emission optical fiber, respectively. The device can be a portable (e.g., handheld) device. The light sensor can comprise a dichroic mirror. The light source can be, for example, a laser light source. The cantilever beam can extend in a first direction, and the indenter can extend away from the cantilever beam in a second direction (which may be perpendicular to the first direction). The device can further comprise a lens disposed adjacent to the light sensor, and an illumination tube disposed adjacent to the lens (and can be configured for area illumination of a target during use, such that spectral imaging can be performed during use). The light sensor (which may comprise the dichroic mirror) can be configured for, for example, spectral imaging and can be (or can be part of) a camera. The cantilever beam can comprise an elastic material. The device can further comprise an electronic unit that comprises the light source, a spectrometer, and/or a microprocessor. The electronic unit can be configured to perform spectroscopic measurements of tissue during use. The at least one optical fiber can comprise an optical fiber configured for spectroscopy measurements.

In another embodiment, a method for performing in vivo tissue diagnosis can comprise: providing, to a tissue of a patient, a device as described herein (e.g., having any or all of the features discussed in the previous paragraph); and using the indenter on the tissue and recording a position of the light from the light source on the light sensor (this can be done continuously as the indenter tip is moved along the tissue. The method can further comprise providing light to the tissue from the light source and performing spectroscopy measurements of the tissue using the spectrometer (see also FIG. 2).

DETAILED DESCRIPTION

Embodiments of the subject invention provide novel and advantageous systems, devices, and methods for in vivo tissue diagnosis. Optical spectroscopy can be utilized to characterize the morphological and/or compositional characteristics of in vivo tissue, and an indentation method can be used to measure the mechanical characteristics of the tissue. These intrinsic properties can then be used to detect disease and/or injury development in the in vivo tissue. A portable (e.g., handheld) device can be used to perform the optical spectroscopy and/or the indentation method.

Embodiments provide a dual-mode tissue diagnostic device, which has he immense clinical potential, particularly in resource-limited settings where access to advanced diagnostic tools is often scarce. The design concept demonstrates high feasibility. A portable (e.g., handheld) device can be capable of performing (and/or configured to perform) concurrent optical spectroscopy and mechanical (indentation) testing on living tissue. By analyzing the intrinsic optical and mechanical properties derived from these tests, the device can detect tissue injuries and/or monitor disease progression. The device can be affordable, user-friendly, and easy to maintain, making it ideally suited for use in low-resource settings and/or for at-home testing.

Embodiments of the subject invention provide real-time tissue diagnosis, which delivers instant evaluations of tissue conditions, allowing clinicians to streamline patient management. As disease progression and injuries cause changes in the intrinsic mechanical and optical properties of tissues, it becomes feasible to develop diagnostic tools that utilize both mechanical and optical testing methods. While some experimental tissue diagnostic tools attempt to use one modality or the other, embodiments of the subject invention provide a tool that operationally combines both modalities. The straightforward design enables easy manufacturing, operation, and maintenance, as well as adaptability to various environments. In addition, systems, methods, and devices of embodiments of the subject invention perform noninvasive tissue diagnosis, which diminishes the physiological trauma patients typically undergo with related art methods, such as biopsies, and facilitates repeated and routine diagnoses.

Figure 1A:
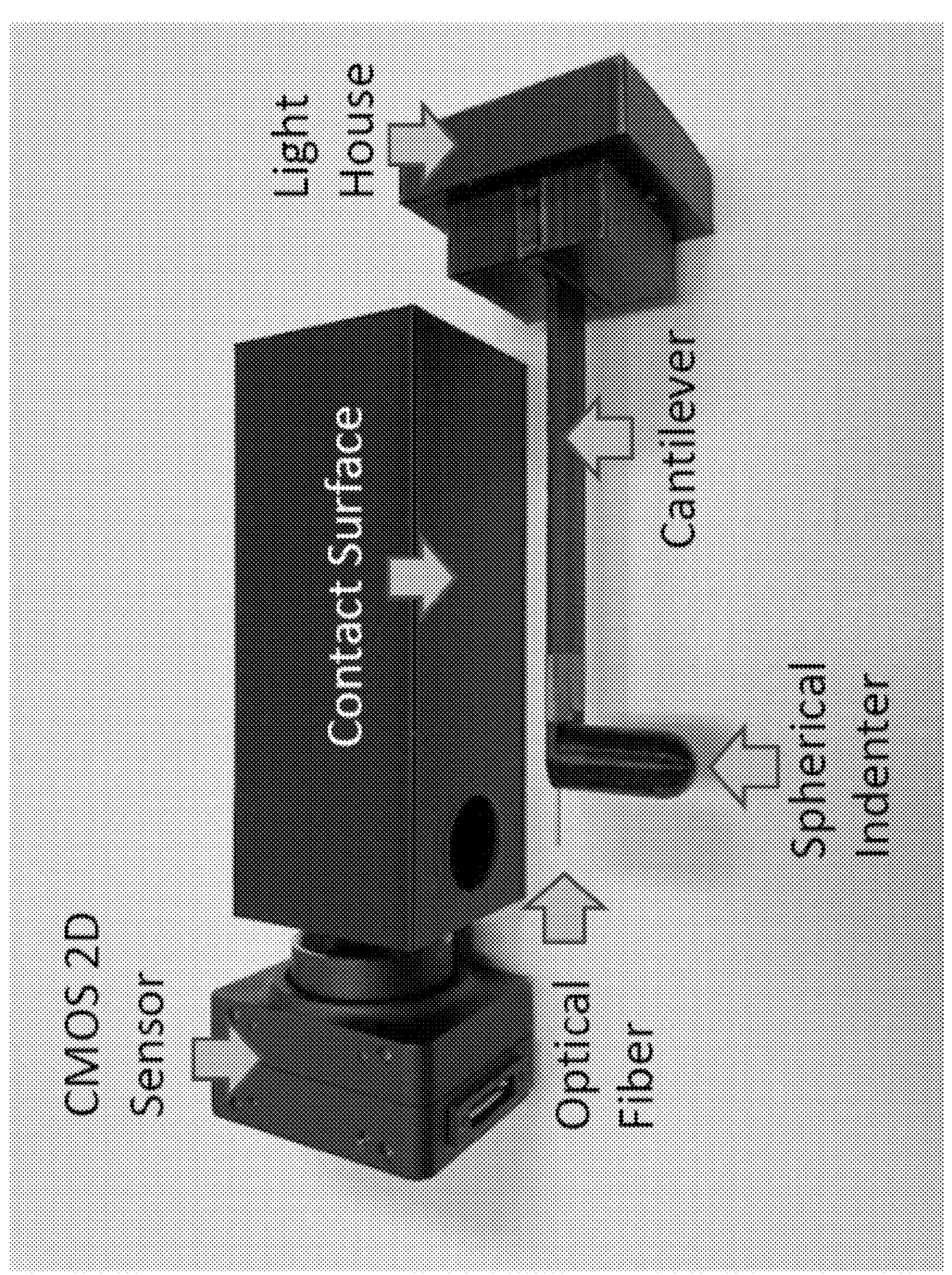
FIG. 1A shows a portable mechanical indenter, according to an embodiment of the subject invention.
Figure 1B:
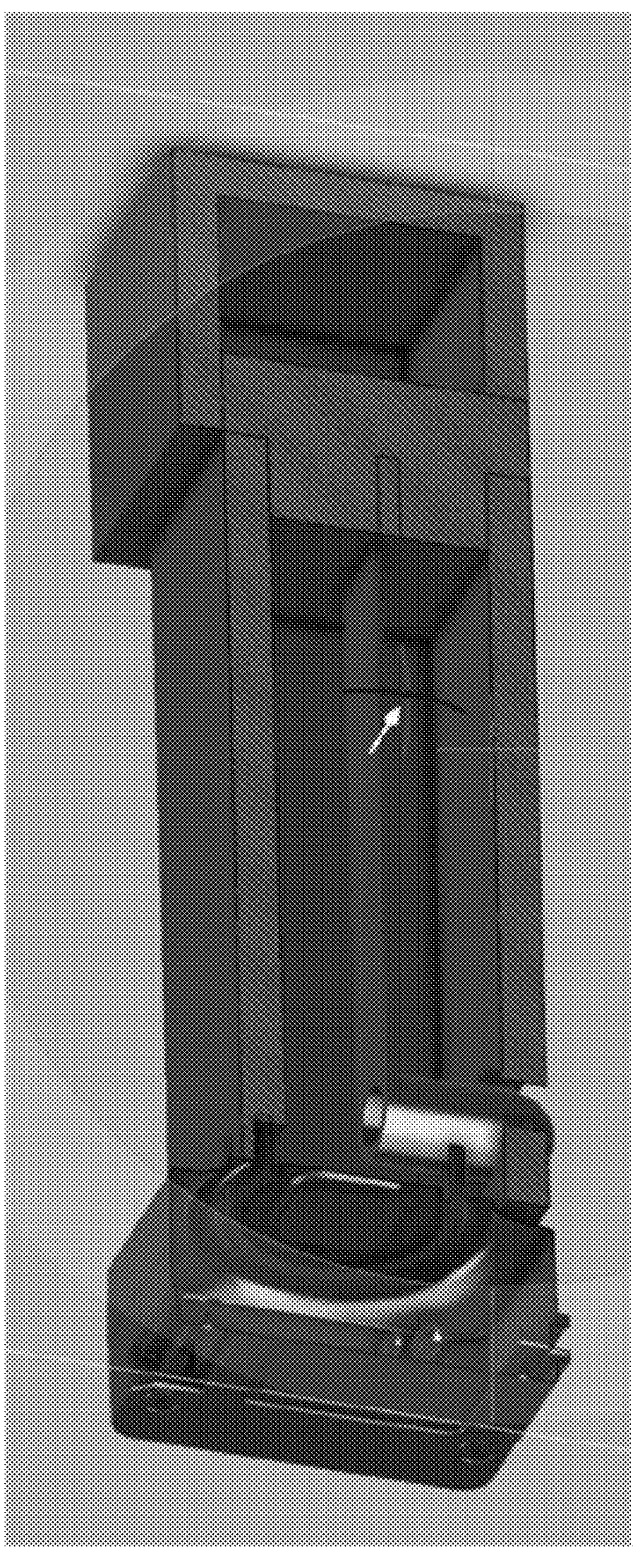
FIG. 1B shows cross-sectional view of a portable mechanical indenter, according to an embodiment of the subject invention.
Figure 1C:
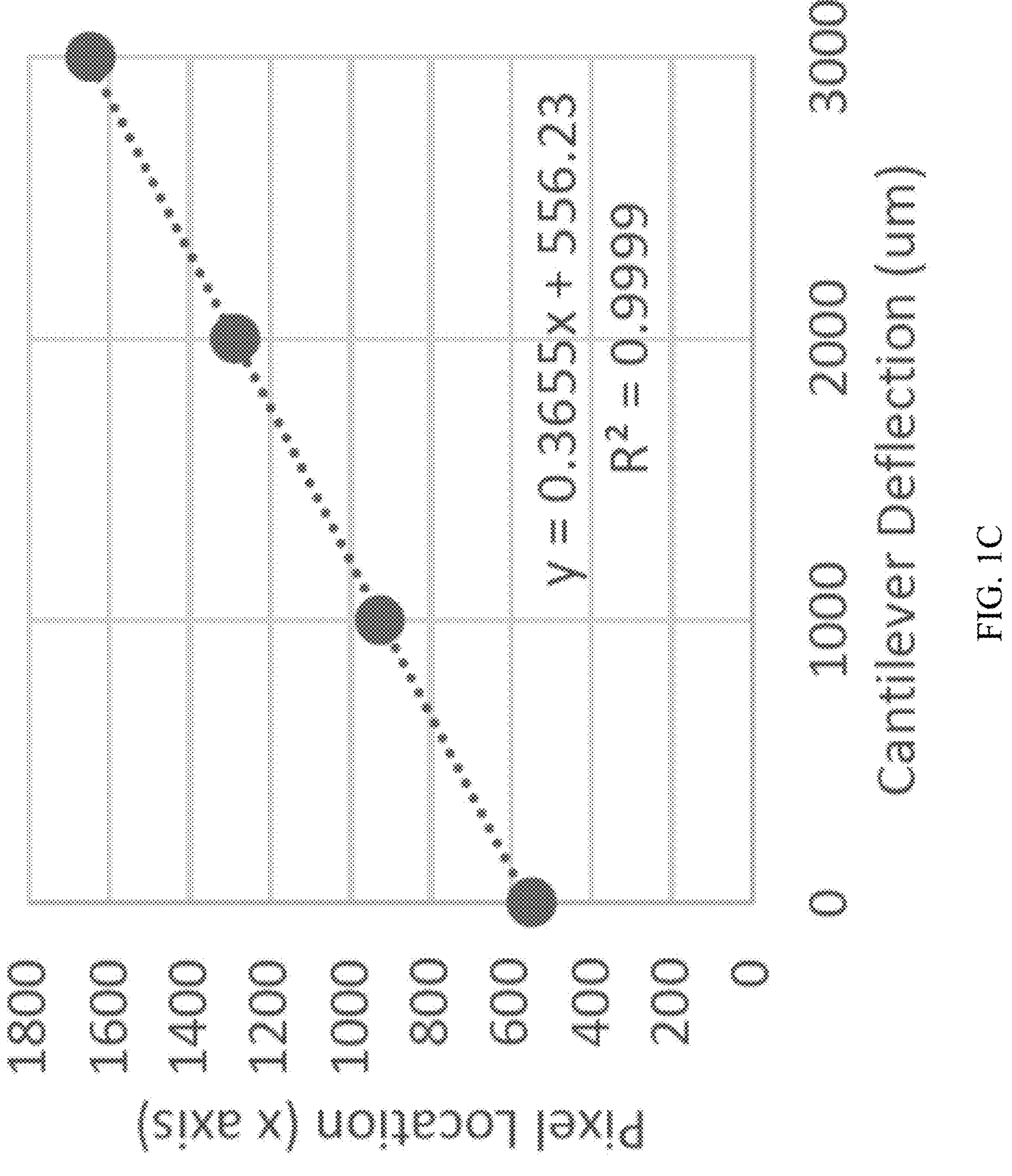
FIG. 1C shows a plot of pixel location (along x-axis) versus cantilever deflection (in micrometers (μm)), showing the relationship between the location of the illuminated spot on a sensor (e.g., a two-dimensional (2D), such as a complementary metal oxide semiconductor (CMOS) 2D sensor) and the deflection of the cantilever beam of a portable mechanical indenter (such as that shown in FIGS. 1A and 1B).

FIG. 1A shows a portable mechanical indenter, according to an embodiment of the subject invention; and FIG. 1B shows cross-sectional view a portable mechanical indenter, according to an embodiment of the subject invention. In order to assess regional elasticity of a sample (e.g., skin of a patient), the indenter can be positioned atop the sample, ensuring full contact between the indenter's surface and the sample. Referring to FIGS. 1A and 1B, the indenter can include a main housing, a light source (e.g., a light-emitting diode (LED)), a light source housing (which can be referred to as a light house) for the light source, an optical fiber, a cantilever (which can be referred to as a cantilever beam), an indenter (e.g., a spherical indenter), and a sensor (e.g., a two-dimensional (2D), such as a complementary metal oxide semiconductor (CMOS) 2D sensor). The indenter can extend from the cantilever (e.g., in a perpendicular direction or approximately perpendicular direction from which the cantilever extends). The optical fiber can be disposed on and/or within the cantilever. The light source housing and the sensor can be disposed on opposite ends of the main housing. The cantilever can be disposed within the main housing, and the indenter can project downwardly from the main housing. The indenter can project downwardly through a hole in a surface (e.g., the surface that contacts the sample in use (which can be referred to as a contact surface)) of the main housing. The light source can emit light (e.g., visible light) that can be channeled through the optical fiber. The light emerging from the optical fiber's distal end (i.e., the end farthest from the light source) can be projected onto the sensor. This configuration can enables the quantification of deflection of the cantilever beam, facilitating an estimation of the indentation depth. FIG. 1C shows results of a calibration study that elucidates the relationship between the location of the illuminated spot on the sensor and the deflection of the cantilever beam.

Figure 2:
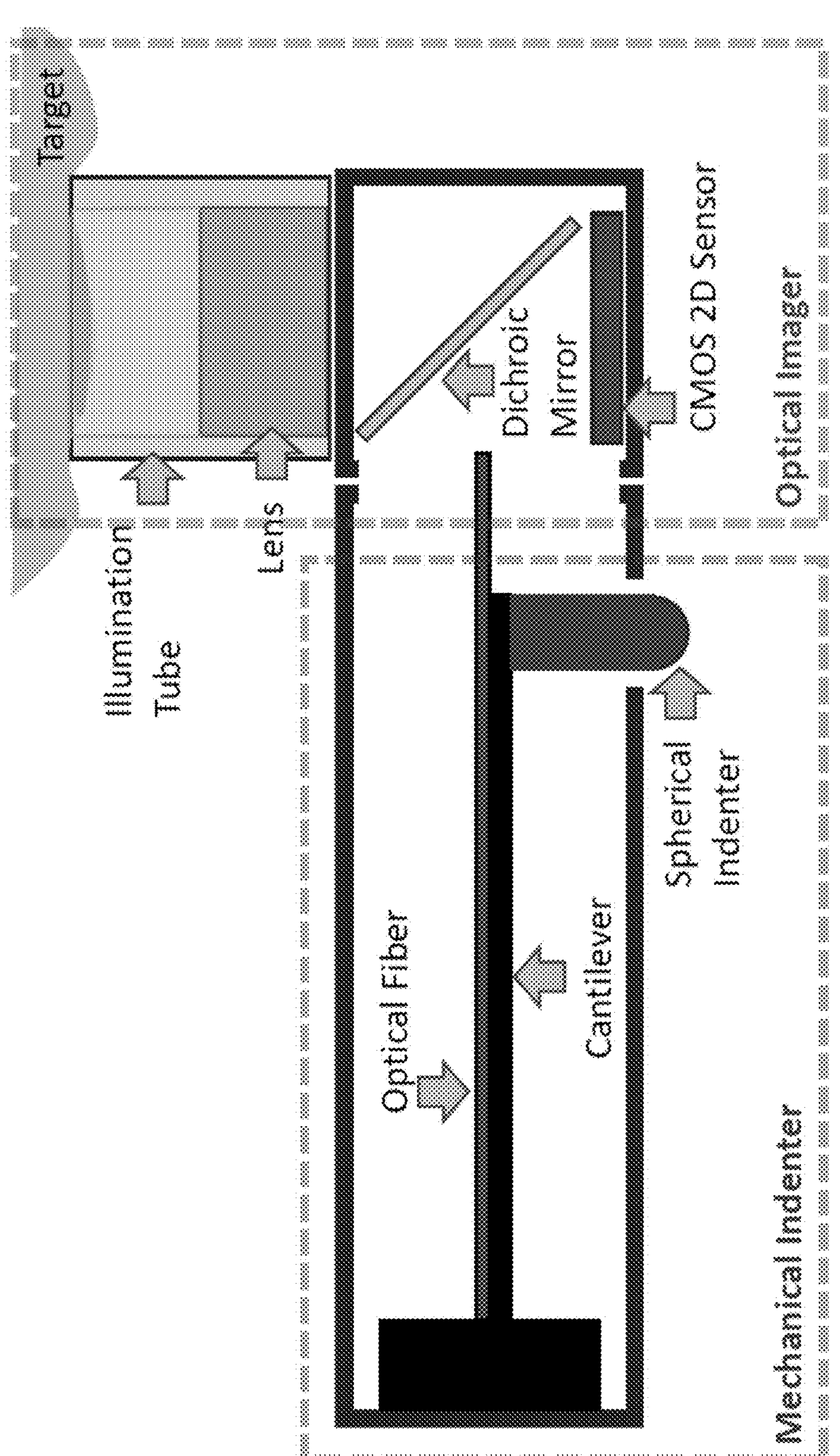
FIG. 2 shows a schematic view of a handheld multimodal device for skin cancer screening, according to an embodiment of the subject invention.
Figures 3A, 3B:
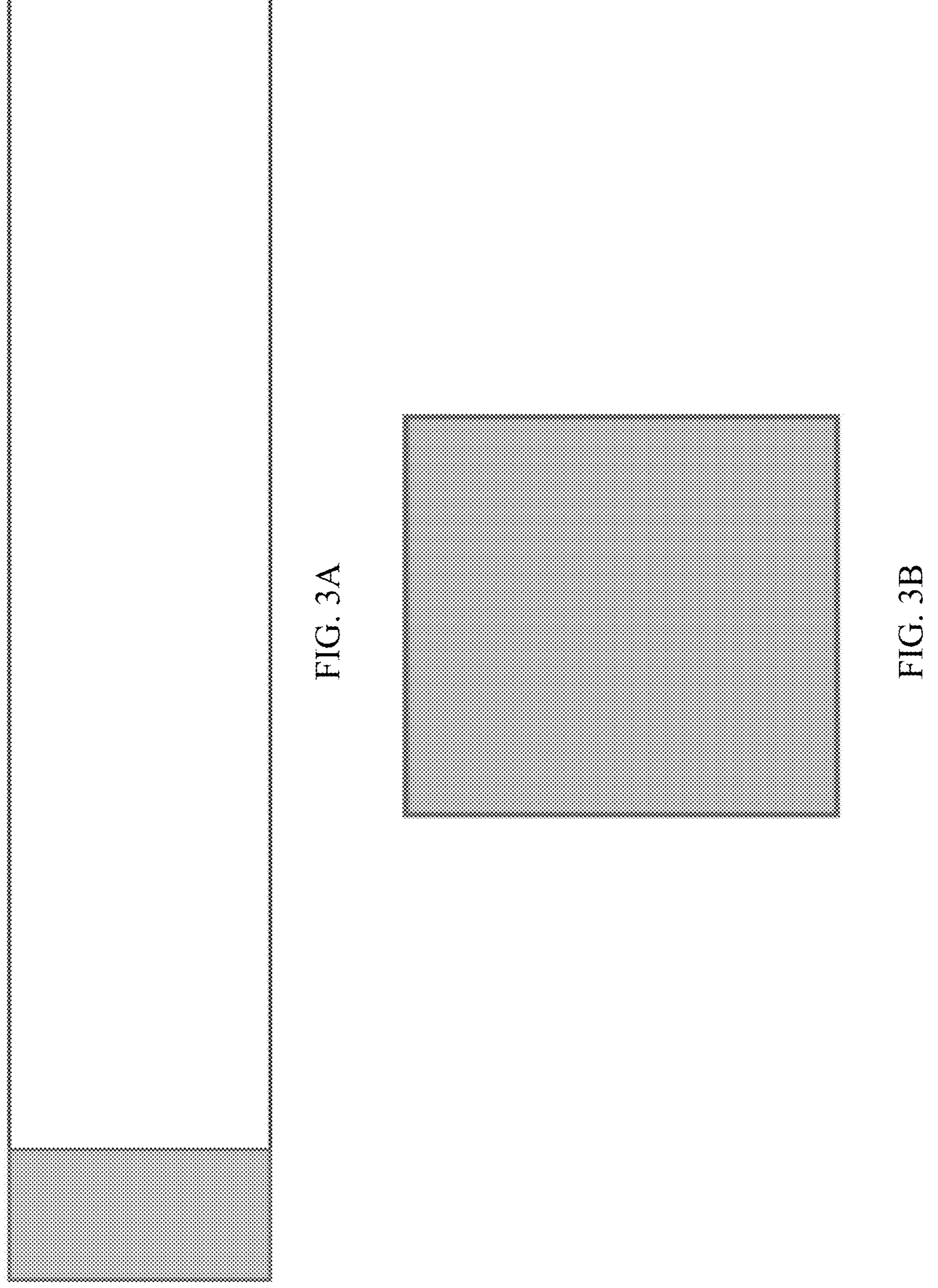
FIG. 3A shows a top view of a handheld multimodal device for skin cancer screening, according to an embodiment of the subject invention.
FIG. 3B shows a front view of the handheld multimodal device from FIG. 3A.
Figures 3C, 3D:
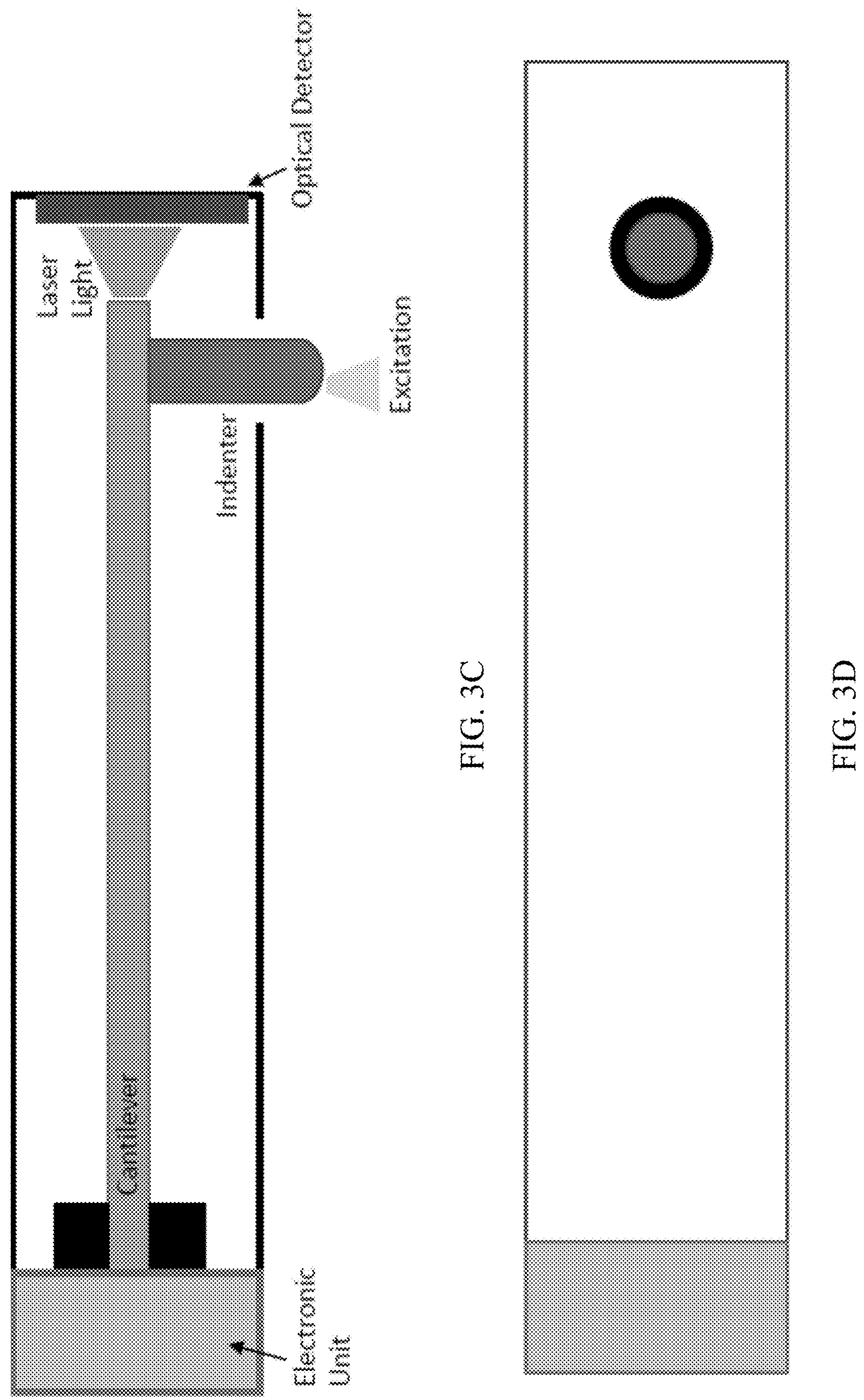
FIG. 3C shows a side view of the handheld multimodal device from FIGS. 3A and 3B.
FIG. 3D shows a bottom view of the handheld multimodal device from FIGS. 3A-3C.

FIG. 2 shows a schematic view of a handheld multimodal device (which can be used for, e.g., skin cancer screening), according to an embodiment of the subject invention. The mechanical indention modality and functionality can be the same as for the device of FIGS. 1A and 1B. The device can include an optical imager configured to discern both visual characteristics and optical properties of skin lesions. The optical imager can include a sensor (e.g., a 2D sensor, such as a CMOS 2D sensor), a mirror (e.g., a dichroic mirror), a lens, and/or an illumination tube. The illumination tube can be configured to provide wavelength-specific trans-illumination. For spectral imaging, the illumination tube can be in direct physical contact with the sample, reducing the typical specular illumination sometimes seen in such imaging. The device can be further enhanced with a modular design for the illumination tube and lens assembly, accommodating lesions of varying sizes.

FIGS. 3A-3D show a top view, a front view, a side view, and a bottom view, respectively, of a handheld multimodal device (which can be used for, e.g., skin cancer screening), according to an embodiment of the subject invention. The cantilever can be configured to apply an indentation force to a tip of the indent. It can house one or more optical fibers used for position sensing and/or optical diagnosis (i.e., spectroscopy). The indenter can serve as the interface between the device and the sample (e.g., tissue or skin). Mechanical and optical tests can be conducted at the tip of the indenter. Light (e.g., laser light) can be emitted from one of the optical fibers within the cantilever, and the light can be utilized to measure the indenter's displacement. The device can include an electronic unit having the light source (or can include a standalone light source). The optical detector can detect the light to measure the indenter's displacement. The electronic unit can house the light source (e.g., laser light source), a spectrometer, and/or a microprocessor. The electronic unit can be configured to acquire spectroscopic data and/or process a response of the optical detector.

Figures 4A, 4B:
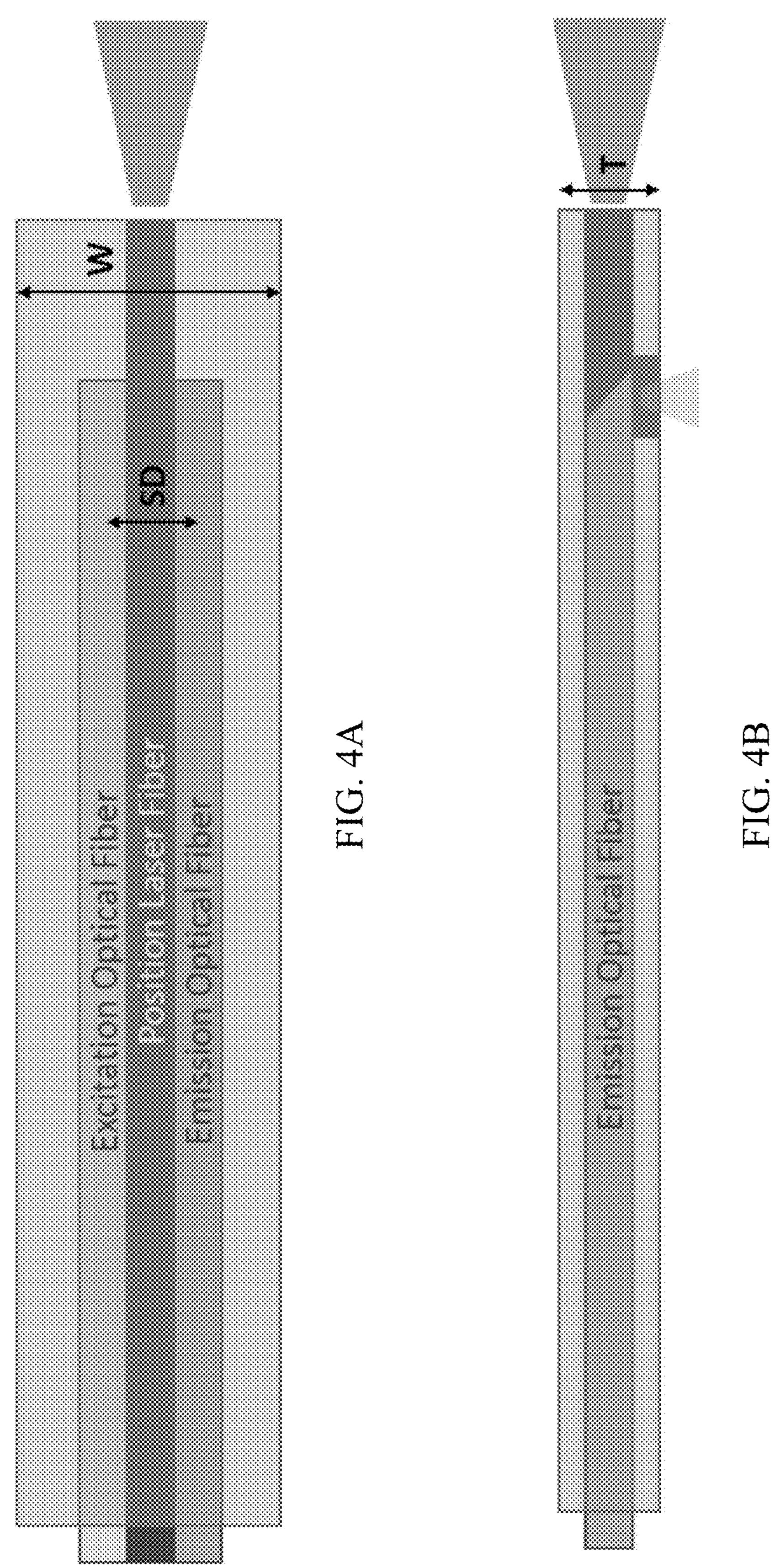
FIG. 4A shows a top view of a cantilever that can be used in a device, according to an embodiment of the subject invention.
FIG. 4B shows a side view of the cantilever from FIG. 4A.

FIGS. 4A and 4B show a top view and a side view, respectively, of a cantilever that can be used in a device, according to an embodiment of the subject invention. The cantilever can be spectroscopy-ready. In some embodiments, the base material of the cantilever can be elastic (e.g., an elastic polymer) with known mechanical properties. Its main function can be to support indentation tests. One or more optical fibers can be embedded within the cantilever, with the center optical fiber one used for indenter position measurement (see also FIGS. 5A-5C), while the others (if present) can be used to perform spectroscopy measurements. The cantilever can include connectors (e.g., 90-degree connectors) at the tips of the excitation and emission optical fibers, enabling light transmission between these fibers and those inside the indenter.

Figures 5A, 5B:
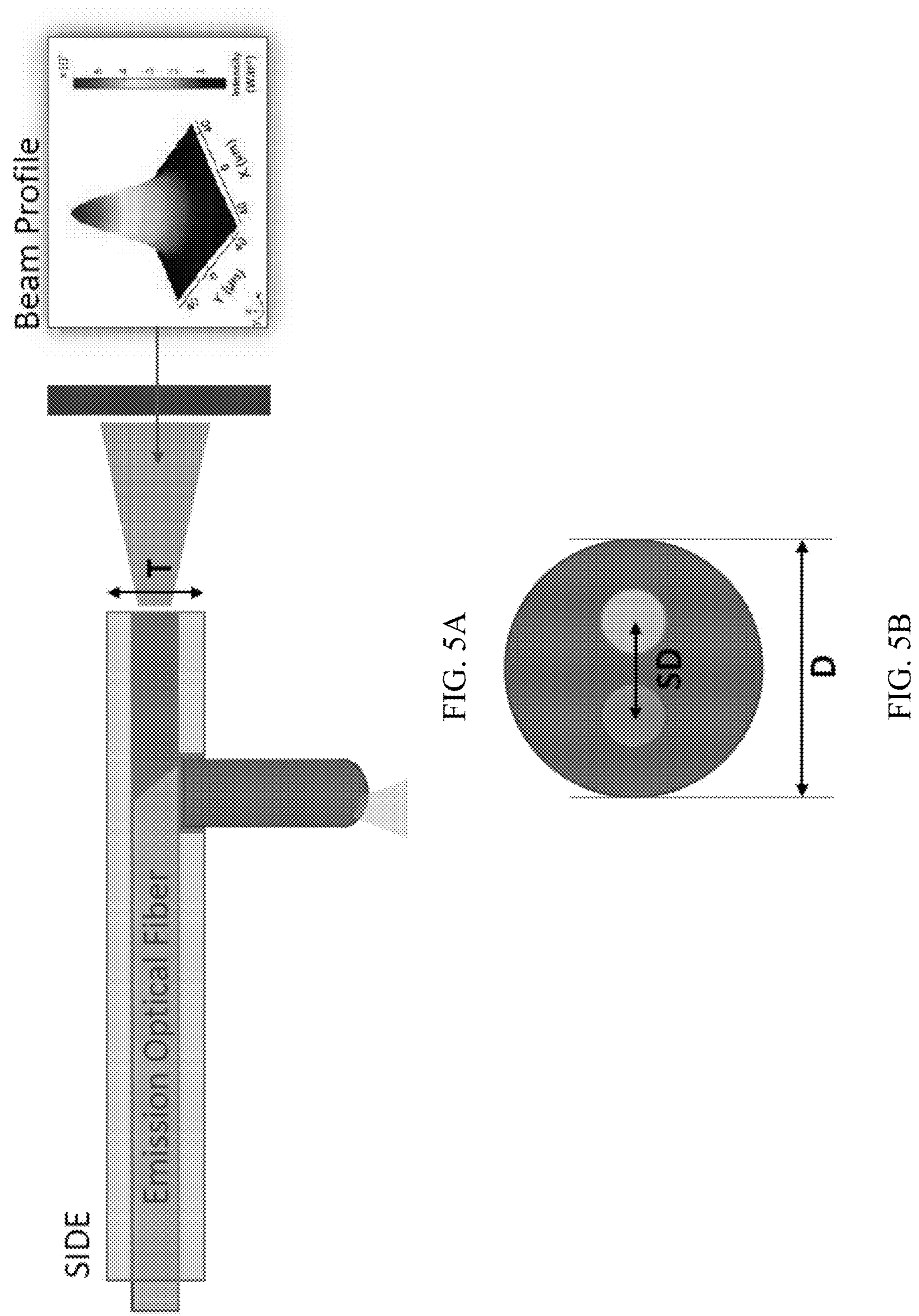
FIG. 5A shows a top view of an indenter and displacement reader that can be used in a device, according to an embodiment of the subject invention. The left-hand portion of FIG. 5A shows a side view of the indenter (extending downward from the right-hand section of the emission optical fiber) and displacement reader (e.g., an optical detector (the vertical rectangular bar just to the left of the "Beam Profile")). The right-hand portion of FIG. 5A shows a beam profile of the beam produced by the indenter.
FIG. 5B shows a bottom view of the indenter from FIG. 5A.
Figure 5C:
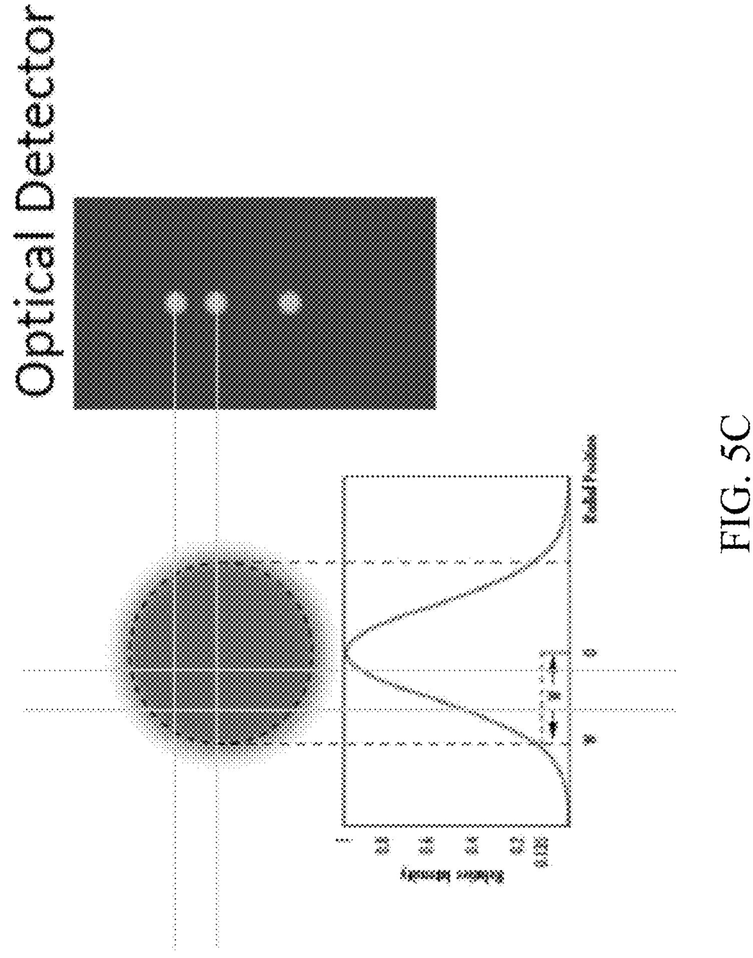
FIG. 5C shows the optical detector from FIG. 5A in the right-hand portion thereof. The left-hand portion of FIG. 5C shows a plot of relative intensity versus radial position, showing the intensity profile of the light (e.g., laser light) emitted by the position laser fiber (see also FIG. 4A).

FIG. 5A shows a top view of an indenter and displacement reader that can be used in a device, according to an embodiment of the subject invention. The left-hand portion of FIG. 5A shows a side view of the indenter (extending downward from the right-hand section of the emission optical fiber) and displacement reader (e.g., an optical detector). The right-hand portion of FIG. 5A shows a beam profile of the beam produced by the indenter. FIG. 5B shows a bottom view of the indenter from FIG. 5A. FIG. 5C shows the optical detector from FIG. 5A in the right-hand portion thereof. The left-hand portion of FIG. 5C shows a plot of relative intensity versus radial position, showing the intensity profile of the light (e.g., laser light) emitted by the position laser fiber (see also FIG. 4A). The indenter can have a spherical tip, and its diameter (D) may be adjusted to accommodate a broad range of tissue mechanical properties. The indenter can include two or more optical fibers for spectroscopy measurements. The distance (SD) between the excitation and the emission fibers can be adjusted for different investigation depths. The indenter tip can include holes for the optical fibers (e.g., the excitation and the emission fibers) to provide light to the sample (e.g., tissue and/or skin of a patient) during use and/or to collect light reflected by the target/sample during use (i.e., the emission optical fiber). The optical detector can include at least one photodiode (e.g., at least three photodiodes strategically placed along the vertical axis) to measure the intensity profile of the light (e.g., laser light) emitted by the position laser fiber (see also FIG. 4A). The displacement of the indenter can cause the vertical shift of the position of the light (e.g., laser light), which can then be quantified by the responses of the optical detector.

Figure 6A:
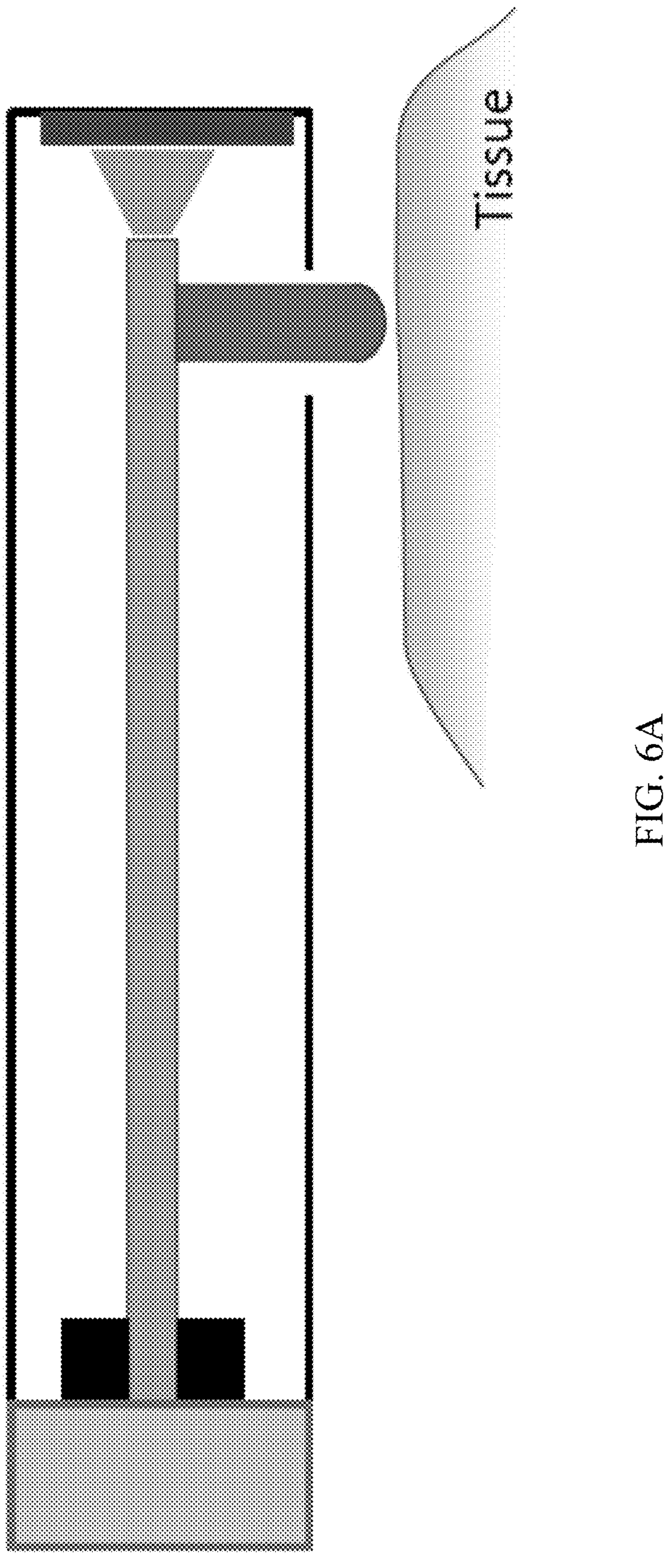
FIG. 6A shows a side view of a handheld multimodal device for skin cancer screening, according to an embodiment of the subject invention, in use on in vivo tissue of a patient.
Figure 6B:
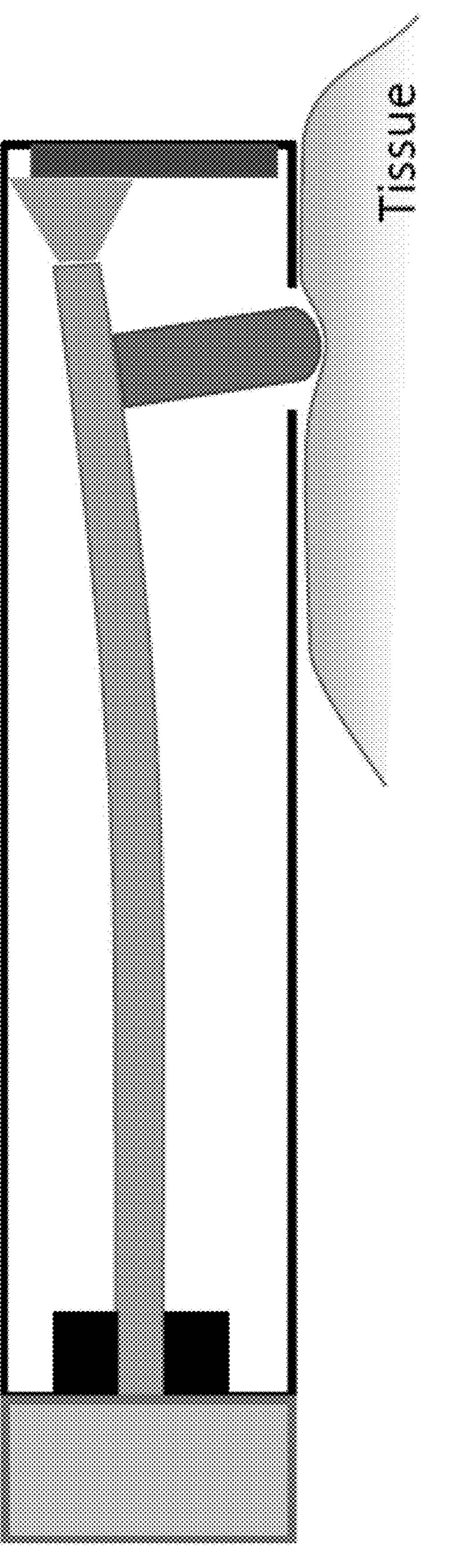
FIG. 6B shows a side view of a handheld multimodal device for skin cancer screening, according to an embodiment of the subject invention, in use on in vivo tissue of a patient.

FIGS. 6A and 6B show side views of a handheld multi-modal device (which can be used for, e.g., skin cancer screening), according to an embodiment of the subject invention, in use on in vivo tissue of a patient. The device can operate similarly to an indentation device. When placed on top of the target tissue, the indenter can produce a small indentation at its tip, reflecting the tissue's mechanical properties, particularly its elasticity. The displacement of the indenter can be measured in order to estimate these mechanical properties of the tissue. Optical fibers embedded within the indenter and cantilever can enable optical investigation of the target tissue. Spectroscopy measurements (e.g., including fluorescence and/or diffuse reflectance) can be carried out to examine the compositional and morphological characteristics of the tissue.

Embodiments of the subject invention provide handheld skin cancer screening devices configured to capture high-definition images of skin lesions, acquire their optical characteristics through multispectral imaging, and assess their mechanical properties via indentation. These collected features can be subjected to sophisticated algorithms for accurate skin lesion classification. Leveraging the intrinsic mechanical properties for skin cancer screening is uncommon in the art, and this additional feature helps to mitigate the skin tone biases often associated with optical technologies used for cancer screening. Embodiments are user-friendly and affordable, facilitating at-home screening. By integrating the device with existing telehealth networks, a robust frontline for skin cancer screening and diagnosis can be established.

Embodiments provide a robust initial screening mechanism for skin cancer by integrating a novel skin cancer detection device with telehealth and/or artificial (AI) technologies. A handheld mechanical indenter (see also FIGS. 1A and 1B) can employ both the indentation technique and cantilever beam deflection technique to extract mechanical properties, such as elasticity, from in vivo tissue. The indenter tip can be spherical, though embodiments are not limited thereto. A spherical indenter tip can enable the application of the Hertz theory to correlate indentation depth with applied force and hence extract the elasticity of the material examined. The cantilever and the indenter can be, for example, three-dimensional (3D)-printed (e.g., from polylactic acid (PLA) or other thermal plastic), and the cantilever's bending characteristics can be adjusted by modifying its thickness and/or width. The length of the cantilever can also be tunable to meet specific requirements for force and degree of deflection. An optical fiber setup can be used to track the magnitude of the cantilever deflection.

In order to capture the appearance and optical properties of skin lesions, embodiments can integrate a multispectral imaging modality into the mechanical indenter (see also FIG. 2). The illumination tube can provide trans-illumination at a plurality of specific (predetermined) wavelengths in the near wavelength region, which minimizes the influence of specular reflection during the process of spectral image acquisitions. This approach can enable the documentation of not only the composition and structural characteristics of a skin lesion but also its appearance, a critical biomarker in skin diagnosis. The lens used in the design can have a short working distance and can provide a minimum of 60 degrees of field of view. While capturing the appearance of the skin lesion, the device can produce high-resolution images with a minimum resolution of 2K. The spectral imaging mode can employ pixel binning to generate lower-resolution images, thereby enhancing the signal-to-noise ratio.

In some embodiments, a device can communicate (e.g., wirelessly or via one or more wires (e.g., universal serial bus (USB) wires, such as USB-C cable)) with a computing device (e.g., a laptop computer). For spectral imaging acquisition, a dedicated software program can be used to control the illumination tube (e.g., wavelength and intensity) and the sensor (e.g., gain and exposure time). The software can offer an interactive guide, facilitating precise device positioning and enabling users to capture high-quality spectral images. Further, the software can provide step-by-step instructions for guiding users through the mechanical indentation process while concurrently recording the degree of cantilever deflection during indentation.

The calibration of the mechanical indentation modality of the device can encompass assessments of cantilever elasticity and cantilever deflection (δ). To achieve this, a benchtop bending test system can be utilized. In the calibration process, deflection (δ) can be measured as a function of the contact force (F) applied at the tip of the indenter. The (δ) and F relationship can be converted to elasticity using the standard beam deflection formula, which can then be compared with the manufacturer-reported elasticity of the material used to construct the cantilever. During the calibration procedure, the location (x,y) of the illumination spot on the sensor can be recorded to establish a look-up table of (x,y)

vs δ. This look-up table can be utilized when the device is used on a sample (e.g., tissue and/or skin of a patient).

The properties of the spectral imaging modality of the prototype device can be quantified using a standard procedure, which can include (1) radiometric calibration to determine the accuracy of spectral reproduction and (2) geometric calibration to characterize the intrinsic camera properties. The field of view and spatial resolution of the imaging modality can be measured using standards, such as the USAF 1951 resolution paper target.

The principle of the factorial experimental design can be utilized to design all validation studies to effectively and systematically evaluate the effects of various parameters of the prototype device on its performance. Here, tissue phantoms can be utilized to validate the functionalities of the device. The mechanical tissue phantoms can be constructed using, for example, polydimethylsiloxane (PDMS), and they can be homogenous mechanical-properties-wise. The optical tissue phantoms can include a matrix (e.g., a gelatin matrix) containing absorbers (e.g., food dyes) and scatterers (e.g., polystyrene spheres). In addition to homogenous ones, optical tissue phantoms with surface inhomogeneity (mimicking skin lesions) can be produced. The intrinsic mechanical and optical properties of the phantoms can be measured using the device as well as the established reference methods (e.g., double integrating technique for optical property measurements).

The device's measurements can be compared to those from the reference methods using Bland-Altman plots and linear regression analyses. The difference between the device's measurements and the reference measurements can be analyzed (e.g., using factorial analysis of variance (ANOVA)) to identify device parameters/properties contributing to significant errors in optical and mechanical measurements. The outcomes of the validation studies can confirm the utility of the handheld multimodal device, ensuring both its accuracy and clinical relevance.

Embodiments of the subject invention can help establish baseline characteristics of normal skin, thereby addressing a critical gap in the field of skin cancer diagnosis research. Given the frequent unavailability or difficulty in obtaining data on normal skin tissue, this can serve as an essential foundation for the future development of skin cancer screening algorithms. Optical and mechanical properties of skin can be assessed from a patient using the handheld multimodal device. Measurements can be conducted at multiple anatomical sites, including, for example, the forehead, brachial and antebrachial regions of the arms, chest, back, abdomen, and femoral and tibial regions of the legs. This extensive sampling strategy can help uncover location-dependent variations in the skin's intrinsic optical and mechanical characteristics. In addition to capturing optical and mechanical metrics, demographic and medical parameters such as age, height, weight, and existing medical conditions can be systematically documented for patients. Subsequent data analysis (e.g., employing factorial ANOVA) can be performed to understand the degree of variation in optical and mechanical properties within groups (e.g., racial groups) and across different anatomical sites. A comparative statistical analysis across groups can help to further identify unique optical and mechanical properties specific to each group. A power analysis can be performed to ascertain the minimal sample size required to yield statistically significant differences in these identified features, thereby guiding future research.

Embodiments of the subject invention have transformative potential in the realm of skin cancer screening, especially in high-risk locales such as Florida. Factors like excessive sun exposure and a sizable geriatric demographic amplify the prevalence of skin cancer in these regions. Designed for affordability and ease-of-use, the handheld multimodal device can amplify the frequency of skin lesion screenings. Integration into telehealth infrastructures can help further escalate screening rates, thereby improving the odds of early skin cancer detection. Additionally, the device can be equipped to interface with advanced classification algorithms, streamlining the initial screening process and reducing the clinical workload. This feature not only accelerates the diagnostic timeline but also enriches the training dataset for fine-tuning AI-based skin cancer diagnostic algorithms. Importantly, the device can be engineered to mitigate the inherent skin-tone bias in traditional diagnostic methods, enhancing diagnostic accuracy for individuals with darker skin tones, including Black and Hispanic populations.

Embodiments of the subject invention can be used in, for example, point-of-care diagnostics, regular monitoring, telemedicine, screening programs, emergency medicine, veterinary medicine, medical research, sports medicine, and prosthetics. In point-of-care diagnostics, the device can be utilized in clinics, hospitals, and remote locations for on-the-spot assessment of tissue conditions, allowing for faster and more informed clinical decisions. In regular monitoring, the device enables routine monitoring of chronic conditions and treatment responses without causing discomfort or additional harm to patients, promoting more personalized care. In telemedicine, the non-invasive tissue diagnosis devices can be integrated with telemedicine services to facilitate remote consultations and evaluations, improving healthcare access for rural and underserved populations. In screening programs, the device can be employed for mass screening initiatives, such as early detection of cancer, skin conditions, or other tissue-related diseases, potentially improving health outcomes and reducing healthcare costs. In emergency medicine, portable devices can be used in emergency settings, such as disaster relief or military operations, to quickly assess tissue injuries and inform triage decisions. In veterinary medicine, non-invasive tissue diagnosis can be extended to veterinary medicine for the assessment and monitoring of animal health. In medical research, the device can be a valuable tool in research settings for studying tissue properties, disease progression, and response to various treatments in a non-invasive manner. In sports medicine, portable diagnostic devices can be used for monitoring athletes' tissue health and injury recovery, assisting in the development of personalized training and rehabilitation programs. In prosthetics, the device can facilitate the socket design for prosthetic devices by assessing regional mechanical and hemodynamic characteristics of the stumps.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

When ranges are used herein, combinations and subcombinations of ranges (including any value or subrange contained therein) are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A device for in vivo tissue diagnosis, the device comprising:

a cantilever beam;

an indenter comprising a first end connected to the cantilever beam and an indenter tip at a second end opposite from the first end of the indenter;

a light source configured to provide light;

a plurality of optical fibers disposed on the cantilever beam, the light provided by the light source traveling through the plurality of optical fibers;

a light sensor configured to sense the light provided by the light source; and an electronic unit that comprises the light source, a spectrometer, and a microprocessor the plurality of optical fibers comprising an excitation optical fiber and an emission optical fiber disposed in the indenter, the indenter tip comprising a first hole through which light from the excitation optical fiber exits and a second hole through which light is collected by the emission optical fiber, the electronic unit being configured to perform spectroscopic measurements of tissue during use, the plurality of optical fibers further comprising an optical fiber configured for spectroscopy measurements, the light sensor being configured for spectral imaging, and the light sensor comprising a dichroic mirror.

2. The device according to claim 1, further comprising a main housing in which the cantilever beam is disposed.

3. The device according to claim 2, the electronic unit being disposed at a first end of the main housing, and the light sensor being disposed at a second end of the main housing opposite from the first end of the main housing.

4. The device according to claim 2, the main housing comprising a hole through which the indenter protrudes.

5. The device according to claim 1, the indenter tip being a spherical indenter tip.

6. The device according to claim 1, the device being a handheld device.

7. The device according to claim 1, the light source being a laser light source.

8. The device according to claim 1, the cantilever beam extending in a first direction, and the indenter extending away from the cantilever beam in a second direction perpendicular to the first direction.

9. The device according to claim 1, further comprising:

a lens disposed adjacent to the light sensor; and an illumination tube disposed adjacent to the lens and configured to provide area illumination to a target area during use.

10. The device according to claim 1, the cantilever beam comprising an elastic material.

11. A method for performing in vivo tissue diagnosis, the method comprising:

providing, to a tissue of a patient, the device according to claim 1, using the indenter on the tissue and recording a position of the light from the light source on the light sensor; and providing light to the tissue from the light source and performing spectroscopy measurements of the tissue using the spectrometer.

12. A method for performing in vivo tissue diagnosis, the method comprising:

providing, to a tissue of a patient, the device according to claim 1; and using the indenter on the tissue and recording a position of the light from the light source on the light sensor.

13. A device for in vivo tissue diagnosis, the device comprising:

a cantilever beam;

an indenter comprising a first end connected to the cantilever beam and an indenter tip at a second end opposite from the first end of the indenter;

a light source configured to provide light;

a plurality of optical fibers disposed on the cantilever beam, the light provided by the light source traveling through the plurality of optical fibers;

a light sensor configured to sense the light provided by the light source;

a main housing in which the cantilever beam is disposed;

a lens disposed adjacent to the light sensor;

an illumination tube disposed adjacent to the lens; and an electronic unit that comprises the light source, a spectrometer, and a microprocessor, the electronic unit being disposed at a first end of the main housing, the light sensor being disposed at a second end of the main housing opposite from the first end of the main housing, the main housing comprising a hole through which the indenter protrudes, the plurality of optical fibers comprising an excitation optical fiber and an emission optical fiber disposed in the indenter, the indenter tip comprising a first hole through which light from the excitation optical fiber exits and a second hole through which light is collected by the emission optical fiber, the cantilever beam comprising an elastic material, the electronic unit being configured to perform spectroscopic measurements of tissue during use, and the plurality of optical fibers further comprising an optical fiber configured for spectroscopy measurements.

14. A method for performing in vivo tissue diagnosis, the method comprising:

providing, to a tissue of a patient, the device according to claim 13;

using the indenter on the tissue and recording a position of the light from the light source on the light sensor; and providing light to the tissue from the light source and performing spectroscopy measurements of the tissue using the spectrometer.

* * * * *